United States Patent [19]

Stiefel et al.

[11] Patent Number: 5,017,366

[45] Date of Patent: May 21, 1991

[54] PHARMACEUTICAL COMPOSITIONS

[75] Inventors: Werner K. Stiefel, Coral Gables, Fla.; Charles F. Breunig, Greenville, N.Y.

[73] Assignee: Stiefel Laboratories, Inc., Coral Gables, Fla.

[21] Appl. No.: 522,648

[22] Filed: May 14, 1990
(Under 37 CFR 1.47)

Related U.S. Application Data

[63] Continuation-in-part of Ser. No. 291,670, Dec. 29, 1988, abandoned.

[51] Int. Cl.$^5$ .................. A61K 7/40; A61K 7/42; A61K 7/44; A61K 31/075
[52] U.S. Cl. .................. 424/59; 424/60; 514/29; 514/859; 514/944
[58] Field of Search .................. 424/59, 60; 514/29

[56] References Cited

U.S. PATENT DOCUMENTS 2,113,374  2/1938  Hall .................. 424/59
4,387,089  6/1983  DePolo .................. 424/59

FOREIGN PATENT DOCUMENTS 1375436  11/1974  United Kingdom .................. 424/59

OTHER PUBLICATIONS

The Merck Index, 1976 9th Ed., pp. 482 and 1080.
Sagarin, Cosmetics, Science and Technology, 1957, pp. 199-204.
Kass, Cosmetics & Toiletries, 3/76, vol. 9, pp. 87, 93 and 94.

*Primary Examiner*—Dale R. Ore
*Attorney, Agent, or Firm*—Mathews, Woodbridge & Collins

[57] ABSTRACT

A topical pharmaceutical composition comprising a mixture of (i) at least one topically acceptable UV absorber in a concentration sufficient to block a substantial quantity of sun-generated UV radiation and (ii) an antibacterially effective amount of erythromycin in (iii) an pharmaceutically acceptable topical carrier. A typical formulation contains about 2.2% of erythromycin, about 8% of octyl p-dimethylaminobenzoate, and about 6% of 2-hydroxy-4-methoxybenzophenone in a mixture of about 3.8% hydroxypropylcellulose in ethanol.

15 Claims, No Drawings

PHARMACEUTICAL COMPOSITIONS

This is a continuation in part of U.S. Pat. Application Ser. No. 291,670 filed on Dec. 29, 1988, now abandoned.

The present invention relates to new pharmaceutical compositions having use as an adjuvant to topical tretinoin and isotretinoin therapy, hereinafter referred to as tretinoin therapy.

Tretinoin therapy of acne (and to a lesser extent isotretinoin therapy) is often combined with antibacterial therapy. Moreover, it now is apparent that those under such therapy should avoid excessive exposure to sunlight. Typically tretinoin is applied in the evening and a topical sunscreen is then prescribed for morning application in addition to application of the antibacterial agent.

The present invention pertains to an adjuvant to tretinoin therapy and in particular to a topical pharmaceutical composition comprising a mixture of (i) at least one topically acceptable UV absorber in a concentration sufficient to block a substantial quantity of sun-generated UV radiation and (ii) an antibacterially effective amount of erythromycin in (iii) an pharmaceutically acceptable topical carrier.

Generally the UV absorber includes at least one of an alkyl ester of p-dimethylaminobenzoic acid and a 2-hydroxybenzophenone. Thus for example the UV absorber can be one or more of amyl p-dimethylaminobenzoate, octyl p-dimethylaminobenzoate, 2,4-dihydroxybenzophenone, 2,2'-dihydroxy-4,4,-dimethoxybenzophenone, and 2-hydroxy-4-methoxybenzophenone. Most preferably the UV absorber includes both an absorber of UV-B radiation such as octyl p-dimethylaminobenzoate and an absorber of UV-A radiation such as 2-hydroxy-4-methoxybenzophenone.

An example of a preferred absorber of UV-B is octyl methoxycinnamate. An example of a preferred absorber of UV-A is butyl methoxydibenzoylmethane.

The amount UV absorber employed will depend upon its effectiveness in this regard but in any event will be sufficient to block a substantial quantity of sun-generated UV radiation. Thus for example when the UV absorber is octyl p-dimethylaminobenzoate, the amount will be from about 4% to about 12% by weight of composition whereas when the UV absorber is 2-hydroxy-4-methoxybenzophenone, the amount will be from about 3% to about 10% by weight of composition.

When the UV-B absorber is octyl methoxycinnamate, the amount employed will be from about 1% to from about 10%, preferably 7% by weight of composition. When the UV-A absorber is butyl methoxydibenzoylmethane, the amount employed is from about 0.1% to from about 5%, preferably 3% by weight of composition.

The amount of erythromycin present will be from about 1.5% to about 3% by weight of composition, as for example about 2%, optionally with a 10% excess, e.g., 2.2%.

The pharmaceutically acceptable topical carrier preferably is an alcoholic gel vehicle as for example a mixture of hydroxypropylcellulose in ethanol. Typically the amount will be from about 3.5 to about 4% of hydroxypropylcellulose in ethanol and this carrier will comprise at least 80% by weight of the composition.

A particularly preferred composition employs about 2.2% by weight of composition of erythromycin together with about 8% by weight of composition of octyl p-dimethylaminobenzoate and about 6% by weight of composition of 2-hydroxy-4-methoxybenzophenone in a carrier consisting of about 81% ethanol and about 3% of hydroxypropylcellulose, both by weight of composition. Pharmaceutically acceptable dyes, fragrances, and/or antioxidants also can be included. The optional incorporation of one or more dyes producing a greenish color, for example, will tend to mask residual redness of the lesion.

A further preferred composition employs about 2.2% by weight of composition of erythromycin together with about 3% by weight of composition of butyl methoxydibenzoylmethane and about 6% by weight of composition of 2-hydroxy-4-methoxybenzophenone in a carrier consisting of about 86% ethanol and about 3% of hydroxypropylcellulose, both by weight of composition. Pharmaceutically acceptable dyes, fragrances, and/or antioxidants also can be included. Again, the optional incorporation of one or more dyes producing a greenish color, for example, will tend to mask residual redness of the lesion.

Yet another preferred composition employs about 2% by weight of composition of erythromycin together with about 7% by weight of composition of octyl methoxycinnamate and about 6% by weight of composition of 2-hydroxy-4-methoxybenzophenone together with 9.5% by weight of composition of a pharmaceutically acceptable perfume and 9.5% by weight of a pharmaceutically acceptable colorant in a carrier consisting of about 63% ethanol and about 3% of hydroxypropylcellulose, both by weight of composition.

The composition is prepared by combining the indicated components and then thoroughly blending the same to produce the desired gel.

In practice, the composition is simply applied to the acne lesion which has previously received tretinoin therapy. Ideally the tretinoin therapy is effected in the prior evening and the present composition then is applied in the morning.

The following examples are representative.

EXAMPLE 1

| Ingredient | | % Total Comp. |
|---|---|---|
| Octyl p-dimethylaminobenzoic acid ("Escalol 507") | | 8.0000 |
| 2-Hydroxy-4-methoxybenzophenone ("Uvinul M-40") | | 6.0000 |
| Erythromycin U.S.P. | | 2.2000 |
| Hydroxypropylcellulose ("Klucel HF") | | 3.0000 |
| FD & C Green #3 | | 0.0015 |
| D & C Yellow #10-9284 | | 0.0003 |
| Ethanol (SD alcohol 40B) | q.s. to | 100.0000 |

The foregoing ingredients are combined and thoroughly blended to produce a gel. A small amount of the gel is applied once in the morning to acne lesions which previously have been subjected to tetrinoin therapy.

EXAMPLE 2

The foregoing ingredients are combined and thoroughly blended to produce a gel. A small amount of the gel is applied once inn the morning to acne lesions which previously have been subjected to tetrinoin therapy.

EXAMPLE 2

| Ingredient | | % Total Comp. |
|---|---|---|
| Amyl p-dimethylaminobenzoic acid ("Escalol 506") | | 8.0000 |
| 2-Hydroxy-4-methoxybenzophenone ("Escalol 567") | | 6.0000 |
| Erythromycin U.S.P. | | 2.2000 |
| Hydroxypropylcellulose ("Klucel HF") | | 3.0000 |
| Ethanol (SD alcohol 40B) | q.s. to | 100.0000 |

The foregoing ingredients are combined and thoroughly blended to produce a gel. A small amount of the gel is applied once in the morning to acne lesions which previously have been subjected to tretinoin therapy.

EXAMPLE 3

| Ingredient | | % W/W |
|---|---|---|
| 2-Hydroxy-4-methoxybenzophenone ("Escalol 567") | | 6.00 |
| Butyl Methoxydibenzoylmethane (Parsol 1789) | | 3.00 |
| Hydroxypropylcellulose (Klucel HF) | | 3.00 |
| Erythromycin, USP | | 2.20 |
| Ethanol (SD Alcohol 40B) | q.s to | 100.00 |

The foregoing ingredients are combined and thoroughly blended to produce a gel. A small amount of the gel is applied once in the morning to acne lesions which previously have been subjected to tretinoin therapy.

EXAMPLE 4

| Ingredient | | % W/W |
|---|---|---|
| Octyl Methoxycinnamate (Parsol MCX) | | 7.00 |
| 2-Hydroxy-4-methoxybenzophenone ("Escalol 567") | | 6.00 |
| Hydroxypropylcellulose (Klucel HF) | | 3.00 |
| Erythromycin, USP | | |
| Perfume | | 9.50 |
| Colorant | | 9.50 |
| Ethanol (SD Alcohol 40B) | q.s. to | 100.00 |

The foregoing ingredients are combined and thoroughly blended to produce a gel. A small amount of the gel is applied once in the morning to acne lesions which previously have been subjected to tretinoin therapy.

What is claimed is:

1. A topical pharmaceutical composition comprising a mixture of (i) at least one topically acceptable UV absorber in a concentration sufficient to block a substantial quantity of sun-generated UV radiation and (ii) an antibacterially effective amount of erythromycin in (iii) an pharmaceutically acceptable topical carrier.

2. A topical pharmaceutical composition according to claim 1 wherein the pharmaceutically acceptable topical carrier is an alcoholic gel vehicle.

3. A topical pharmaceutical composition according to claim 1 wherein the UV absorber includes at least one of an alkyl ester of p-dimethylaminobenzoic acid and a 2-hydroxybenzophenone.

4. A topical pharmaceutical composition according to claim 1 wherein the UV absorber includes at least one of octyl p-dimethylaminobenzoate and 2-hydroxy-4-methoxybenzophenone.

5. A topical pharmaceutical composition according to claim 1 wherein the UV absorber includes both octyl p-dimethylaminobenzoate and 2-hydroxy-4-methoxybenzophenone.

6. A topical pharmaceutical composition according to claim 1 wherein the amount of erythromycin is from about 1.5% to about 3% by weight of composition.

7. A topical pharmaceutical composition according to claim 1 wherein the UV absorber includes from about 4% to about 12% by weight of composition of octyl p-dimethylaminobenzoate and from about 3% to about 10% by weight of composition of 2-hydroxy-4-methoxybenzophenone.

8. A topical pharmaceutical composition according to claim 7 wherein the pharmaceutically acceptable topical carrier is an alcoholic gel vehicle comprises a mixture of about 3.8% hydroxypropylcellulose in ethanol.

9. A topical pharmaceutical composition according to claim 8 wherein the amount of erythromycin is about 2.2% by weight of composition and the UV absorber consists of about 8% by weight of composition of octyl p-dimethylaminobenzoate and about 6% by weight of composition of 2-hydroxy-4-methoxybenzophenone.

10. A topical pharmaceutical composition according to claim 1 wherein the UV absorber includes butyl methoxydibenzoylmethane.

11. A topical pharmaceutical composition according to claim 1 wherein the UV absorber includes both butyl methoxydibenzoylmethane and 2-hydroxy-4-methoxybenzophenone.

12. A topical pharmaceutical composition according to claim 2 wherein the amount of erythromycin is about 2.2% by weight of composition and the UV absorber consists of about 3% by weight of composition of butyl methoxydibenzoylmethane and about 6% by weight of composition of 2-hydroxy-4-methoxybenzophenone.

13. A topical pharmaceutical composition according to claim 1 wherein the UV absorber includes octyl methoxycinnamate.

14. A topical pharmaceutical composition according to claim 1 wherein the UV absorber includes both octyl methoxycinnamate and 2-hydroxy-4-methoxybenzophenone.

15. A topical pharmaceutical composition according to claim 2 wherein the amount of erythromycin is about 2% by weight of composition and the UV absorber consists of about 7% by weight of composition of octyl methoxycinnamate and about 6% by weight of composition of 2-hydroxy-4-methoxybenzophenone.

* * * * *